(12) United States Patent
Stanford et al.

(10) Patent No.: US 10,145,805 B2
(45) Date of Patent: Dec. 4, 2018

(54) APPARATUS AND METHODS OF INSPECTING CERAMIC HONEYCOMB BODIES

(71) Applicant: Corning Incorporated, Corning, NY (US)

(72) Inventors: Alan Russell Stanford, Eaton, OH (US); Eric Daniel Treacy, Beaver Dams, NY (US); Lei Wang, Horseheads, NY (US)

(73) Assignee: Corning Incorporated, Corning, NY (US)

(*) Notice: Subject to any disclaimer, the term of this patent is extended or adjusted under 35 U.S.C. 154(b) by 0 days.

(21) Appl. No.: 15/528,919

(22) PCT Filed: Nov. 19, 2015

(86) PCT No.: PCT/US2015/061471
§ 371 (c)(1),
(2) Date: May 23, 2017

(87) PCT Pub. No.: WO2016/085737
PCT Pub. Date: Jun. 2, 2016

(65) Prior Publication Data
US 2017/0336332 A1 Nov. 23, 2017

Related U.S. Application Data

(60) Provisional application No. 62/084,355, filed on Nov. 25, 2014.

(51) Int. Cl.
*G01N 21/956* (2006.01)
(52) U.S. Cl.
CPC .............................. *G01N 21/95692* (2013.01)

(58) Field of Classification Search
CPC ............. G01N 21/954; G01N 21/9515; G01N 21/95692; G01N 21/8806; G01B 11/2531;
(Continued)

(56) References Cited

U.S. PATENT DOCUMENTS 5,463,462 A 10/1995 Ohnishi et al.
7,366,340 B1 * 4/2008 Smithgall ........ G01N 21/95692
264/177.12
(Continued)

FOREIGN PATENT DOCUMENTS

JP 2005274179 A 10/2005
JP 2006200957 A 8/2006
(Continued)

OTHER PUBLICATIONS

PCT Search Report and Written Opinion, International Searching Authority. PCT/US2015/061471, dated Jan. 29, 2016, 10 Pages.
(Continued)

*Primary Examiner* — Sang Nguyen (57) ABSTRACT

An inspection apparatus and method to automatically inspect ceramic honeycomb bodies during the manufacturing thereof. The apparatus includes a light source to shine light through channels of the ceramic honeycomb body, a lens to receive at least a portion of the light transmitted through channels of the ceramic honeycomb body, a camera to capture images of the transmitted light, a support chuck to support the honeycomb body, and a controller to receive the captured images, to analyze each captured image, to adjust the support chuck and/or the lens based on the analysis, and to align the ceramic honeycomb body channels and the lens optical axis.

20 Claims, 7 Drawing Sheets

(58) Field of Classification Search
CPC .............. G06T 7/0057; B01D 46/0086; B01D 46/2418
See application file for complete search history.

(56) References Cited

U.S. PATENT DOCUMENTS

| | | | |
|---|---|---|---|
| 7,497,999 B2 | 3/2009 | Ichikawa | |
| 8,421,857 B2* | 4/2013 | Akao | G01B 11/22 |
| | | | 348/92 |
| 9,523,623 B2* | 12/2016 | Blanchard | B01D 46/2418 |
| 2003/0174320 A1* | 9/2003 | Yokoyama | G01N 21/8806 |
| | | | 356/237.6 |
| 2006/0151926 A1* | 7/2006 | Zoeller, III | F01N 3/0222 |
| | | | 264/603 |
| 2007/0091309 A1* | 4/2007 | Kondo | G01N 21/95692 |
| | | | 356/364 |
| 2007/0132988 A1* | 6/2007 | Gargano | B01D 46/0086 |
| | | | 356/237.6 |
| 2010/0045975 A1 | 2/2010 | Zoeller, III et al. | |
| 2010/0218596 A1* | 9/2010 | Poff | B01D 46/0086 |
| | | | 73/37 |
| 2010/0238284 A1 | 9/2010 | Akao et al. | |
| 2011/0116704 A1* | 5/2011 | Zoeller, III | G01N 21/95692 |
| | | | 382/141 |
| 2011/0128370 A1* | 6/2011 | Booth | G01N 21/952 |
| | | | 348/125 |
| 2015/0346114 A1* | 12/2015 | Gregorski | G01N 21/954 |
| | | | 356/241.1 |

FOREIGN PATENT DOCUMENTS

| | | |
|---|---|---|
| JP | 2008139052 A | 6/2008 |
| JP | 2009300455 A | 12/2009 |

OTHER PUBLICATIONS

English Translation of JP2017527732 Office Action dated Jul. 31, 2018, Japan Patent Office, 3 Pgs.

* cited by examiner

APPARATUS AND METHODS OF INSPECTING CERAMIC HONEYCOMB BODIES

This application is a national stage application under 35 U.S.C. § 371 of International Application No. PCT/US2015/06147, filed on Nov. 19, 2015, which claims the benefit of and priority to U.S. Provisional Patent Application Ser. No. 62/084,355 filed on Nov. 25, 2014 contents of these applications are relied upon and incorporated herein by reference in their entireties.

BACKGROUND

Field

Exemplary embodiments of the present disclosure relate to apparatus and methods of manufacturing ceramic honeycomb bodies, more particularly, to apparatus and methods of automatically inspecting ceramic honeycomb bodies in the manufacturing thereof.

Discussion of the Background

After-treatment of exhaust gas from internal combustion engines may use catalysts supported on high-surface area substrates and, in the case of diesel engines and some gasoline direct injection engines, a catalyzed filter for the removal of carbon soot particles. Porous ceramic flow-through honeycomb substrates and wall-flow honeycomb filters may be used in these applications.

The above information disclosed in this Background section is only for enhancement of understanding of the background of the disclosure and therefore it may contain information that does not form any part of the prior art nor what the prior art may suggest to a person of ordinary skill in the art.

SUMMARY

Exemplary embodiments of the present disclosure provide an inspection apparatus to automatically inspect ceramic honeycomb bodies.

Exemplary embodiments of the present disclosure also provide a method of inspecting ceramic honeycomb bodies automatically.

Additional features of the disclosure will be set forth in the description which follows, and in part will be apparent from the description, or may be learned by practice of the disclosure.

An exemplary embodiment discloses an inspection apparatus to automatically inspect a ceramic honeycomb body. The apparatus includes a light source configured to emit light toward a first end of the ceramic honeycomb body, a lens configured to receive at least a portion of the light transmitted through channels of the ceramic honeycomb body, an imaging device configured to capture images of the transmitted light, a support chuck configured to support the honeycomb body, and a controller configured to receive the captured images, to analyze each captured image, to adjust the support chuck based on the analysis, and to align the channels and the lens optical axis based on the analysis.

An exemplary embodiment also discloses an apparatus to manufacture a ceramic honeycomb body. The apparatus comprises an inspection apparatus including a light source configured to emit light toward a first end of the ceramic honeycomb body, a lens configured to receive at least a portion of the light transmitted through channels of the ceramic honeycomb body, an imaging device configured to capture images of the transmitted light, a support chuck configured to support the honeycomb body, and a controller configured to receive the captured images, to analyze each captured image, to adjust the support chuck based on the analysis, and to align the channels and the lens optical axis based on the analysis.

An exemplary embodiment also discloses a method of automatically inspecting a ceramic honeycomb body. The method includes emitting a light toward a first end of the ceramic honeycomb body, at least a portion of the light transmitted through channels of the ceramic honeycomb body, imaging the portion of light through a lens, capturing a plurality of the images at incremental angles between the channels and an optical axis of the lens, analyzing at least a portion of the captured images, and adjusting the ceramic honeycomb body based on the analyzing to align the channels and the lens optical axis.

An exemplary embodiment also discloses a method of manufacturing a ceramic honeycomb body. The method comprises automatically inspecting the ceramic honeycomb body including emitting a light toward a first end of the ceramic honeycomb body, at least a portion of the light transmitted through channels of the ceramic honeycomb body, imaging the portion of light through a lens, capturing a plurality of the images at incremental angles between the channels and an optical axis of the lens, analyzing at least a portion of the captured images, and adjusting the ceramic honeycomb body based on the analyzing to align the channels and the lens optical axis.

It is to be understood that both the foregoing general description and the following detailed description are exemplary and explanatory and are intended to provide further explanation of the disclosure.

BRIEF DESCRIPTION OF THE FIGURES

The accompanying drawings, which are included to provide a further understanding of the disclosure and are incorporated in and constitute a part of this specification, illustrate exemplary embodiments of the disclosure, and together with the description serve to explain the principles of the disclosure.

DETAILED DESCRIPTION

The manufacture of porous ceramic honeycomb bodies may be accomplished by the process of plasticizing ceramic powder batch mixtures, extruding the mixtures through honeycomb extrusion dies to form honeycomb extrudate, and cutting, drying, and firing the extrudate to produce ceramic honeycomb bodies of high strength and thermal durability having channels extending axially from a first end face to a second end face. As used herein a ceramic honeycomb body includes ceramic honeycomb monoliths and ceramic segmented honeycomb bodies.

A co-extruded or an after-applied exterior skin may form an outer axial peripheral surface of the ceramic honeycomb bodies. Each channel of the honeycomb bodies, whether monolithic or segmented, can be plugged at an inlet face or an outlet face to produce a filter. When some channels are left unplugged a partial filter can be produced. The honeycomb body, whether monolithic or segmented, can be catalyzed to produce a substrate. Further, filters and partial filters can be catalyzed to provide multi-functionality. The ceramic honeycomb bodies thus produced are widely used as ceramic catalyst supports in motor vehicle exhaust systems, and as catalyst supports and wall-flow particulate filters for the removal of soot and other particulates from engine exhausts.

Among the commercially successful processes for ceramic honeycomb manufacture are those that utilize large co-rotating twin screw extruders for the mixing and extruding of ceramic honeycomb extrudate. Ram extrusion, pressing, casting, spraying and 3-dimensional printing are other processes for ceramic honeycomb manufacture.

Exemplary embodiments of the disclosure provide an apparatus to automatically inspect honeycomb bodies and a method of automatically inspecting ceramic honeycomb bodies. According to these exemplary embodiments, an apparatus and method are provided that automatically align the part with the optical axis of the inspection system to image the substrate for internal defects.

Work with automated light box systems has revealed that light box methods exhibit poor repeatability if the process lacks a repeatable alignment method. Experience using manual light box inspection as well as laboratory experimentation has demonstrated that the appearance of internal defects varies with small changes in the orientation of the part being inspected. Automatically finding the orientation in space of the parallel channels of the part in a way which is repeatable and accurate was found to provide repeatable images for repeatable image analysis and defect detection.

The extruded porous ceramic honeycomb body having axially extending channels (referred to herein as a part) can be automatically inspected after firing according to exemplary embodiments of the disclosure. Challenges of an automated inspection system overcome by this disclosure include the automated alignment of the part to be inspected with an inspection device and a repeatable automated method for finding defects which may appear, disappear, or change appearance depending on the alignment of the substrate to be inspected. This disclosure provides an apparatus and method of automated optical inspection for internal defects which overcome these challenges.

Figure 1:
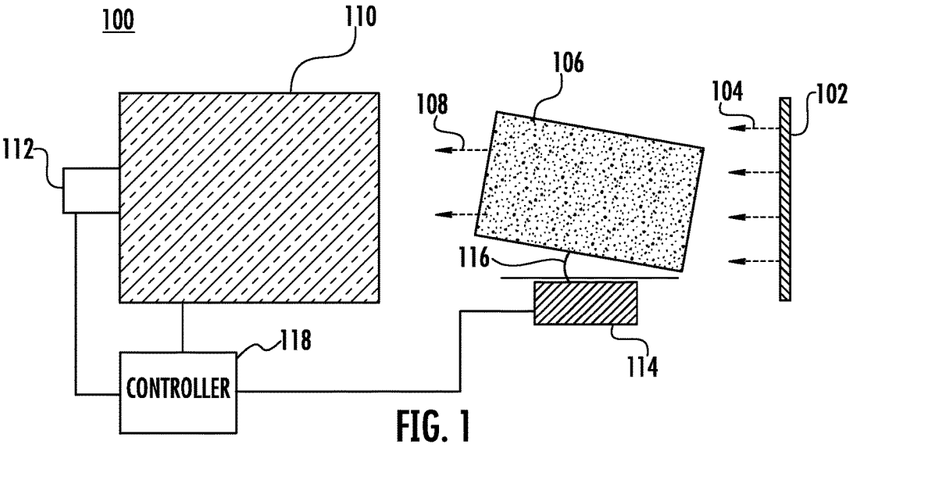
FIG. 1 presents a schematic side view of an inspection apparatus according to exemplary embodiments of the disclosure.

FIG. 1 presents a schematic side view of an inspection apparatus 100 according to exemplary embodiments of the disclosure. As illustrated schematically in FIG. 1, a diffuse light source 102 provides light 104 toward a first face (for example, an inlet face) of the ceramic honeycomb body (part) 106. The diffuse light source 102 (light source) can be a light source transmitted through a diffuser or the diffuse light source 102 can optionally be a collimated light source 102. For example, the diffuse light source 102 can be a light box that has a light emitting surface area greater than an end surface area of the part 106, wherein the end surface area is a cross section through the part 106 that intersects the axial direction of the part 106. The light 108 that is transmitted through the channels of the part is emitted from a second face (for example, an outlet face) of the part 106 toward a telecentric lens 110. The telecentric lens 110 can optionally be a Fresnel lens 110. The telecentric lens 110 (lens) images the light passing through the area (diameter) of the part. For example, the lens 110 can image an area greater than an end surface area of the part 106, wherein the end surface area is a cross section through the part 106 that intersects the axial direction of the part 106.

A camera 112 receiving the image from the lens 110 contains a detector that collects the image. A support chuck 114 provides a support for the part 106 at a vertical reference angle 116. The vertical reference angle 116 may be the angle between the part 106 outer peripheral axial surface and a reference axis extending from the light source 102 to the camera 112, such as along an optical axis of the lens from the light source 102 to the camera 112. The vertical reference angle 116 viewed from the side as in FIG. 1 may be referred to herein as the pitch angle. The collected image may be transmitted from the camera 112 detector to a controller 118 and analyzed.

Figure 2:
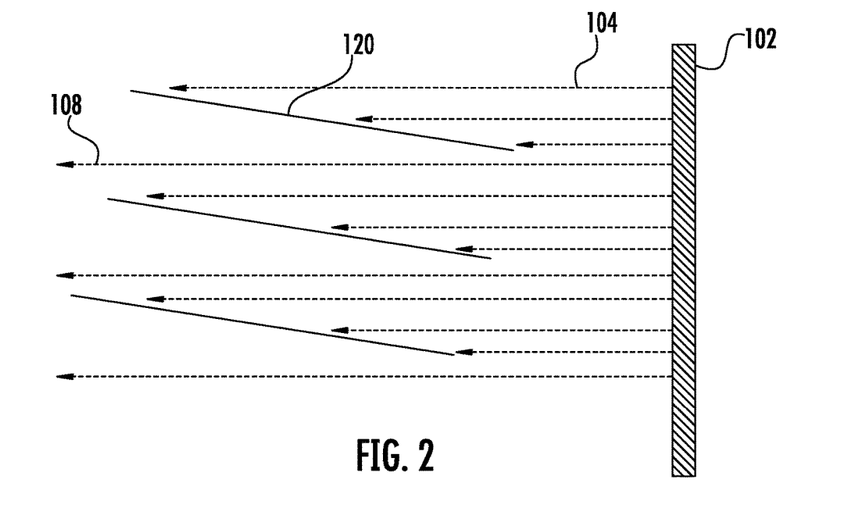
FIG. 2 is a schematic illustration of light from a diffuse light source partially blocked by walls of a ceramic honeycomb body in an inspection apparatus according to exemplary embodiments of the disclosure.

FIG. 2 is a schematic illustration of the light 104 from the light source 102 partially blocked by channel walls 120 of the ceramic honeycomb body at some angle in the inspection apparatus 100 according to exemplary embodiments of the disclosure. While channel walls 120 are generally parallel to the part 106 outer peripheral axial surface they do not have to be as the reference angle 116 is for reference. As illustrated in FIG. 2, a portion of light 108 is transmitted through the honeycomb body channels. As can be seen, when the honeycomb body channels are aligned with the light 104 from the light source 102, the channel walls 120 block less of the light 104 and a greater portion of light 108 is transmitted.

Figure 3:
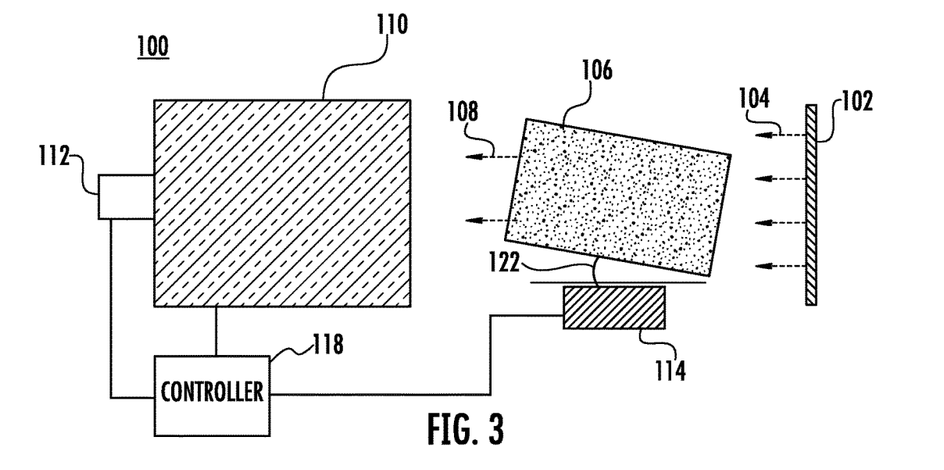
FIG. 3 presents a schematic top view of the inspection apparatus according to exemplary embodiments of the disclosure.

FIG. 3 presents a schematic top view of the inspection apparatus 100 according to exemplary embodiments of the disclosure. As illustrated schematically in FIG. 3, the support chuck 114 provides support for the part 106 at a horizontal reference angle 122. The horizontal reference angle 122 may be the angle between the part 106 outer peripheral axial surface and the reference axis extending from the light source 102 to the camera 112, such as along an optical axis of the lens 110 from the camera 112 to the light source 102. The horizontal reference angle 122 viewed from the top as in FIG. 3 may be referred to herein as the yaw angle.

Figure 4:
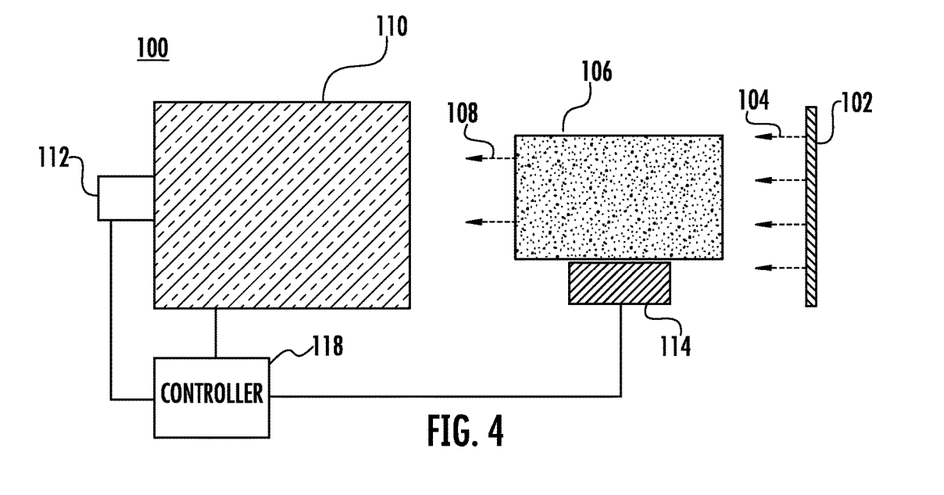
FIG. 4 presents a schematic of the inspection apparatus according to exemplary embodiments of the disclosure.

FIG. 4 presents a schematic of the inspection apparatus 100 according to exemplary embodiments of the disclosure.

FIG. 4 can be a side view or top view after an alignment process such that an average of the channels 120 are aligned with the optical axis of the lens 110. Accordingly, a transport device such as a conveyor, support, or robot arm, can place the part 106 on the support chuck 114 askew of alignment with the lens optical axis, for example, having a pitch angle 116 and/or a yaw angle 122, and the inspection apparatus 100 can automatically align the channels 120 with the lens optical axis.

Figure 5:
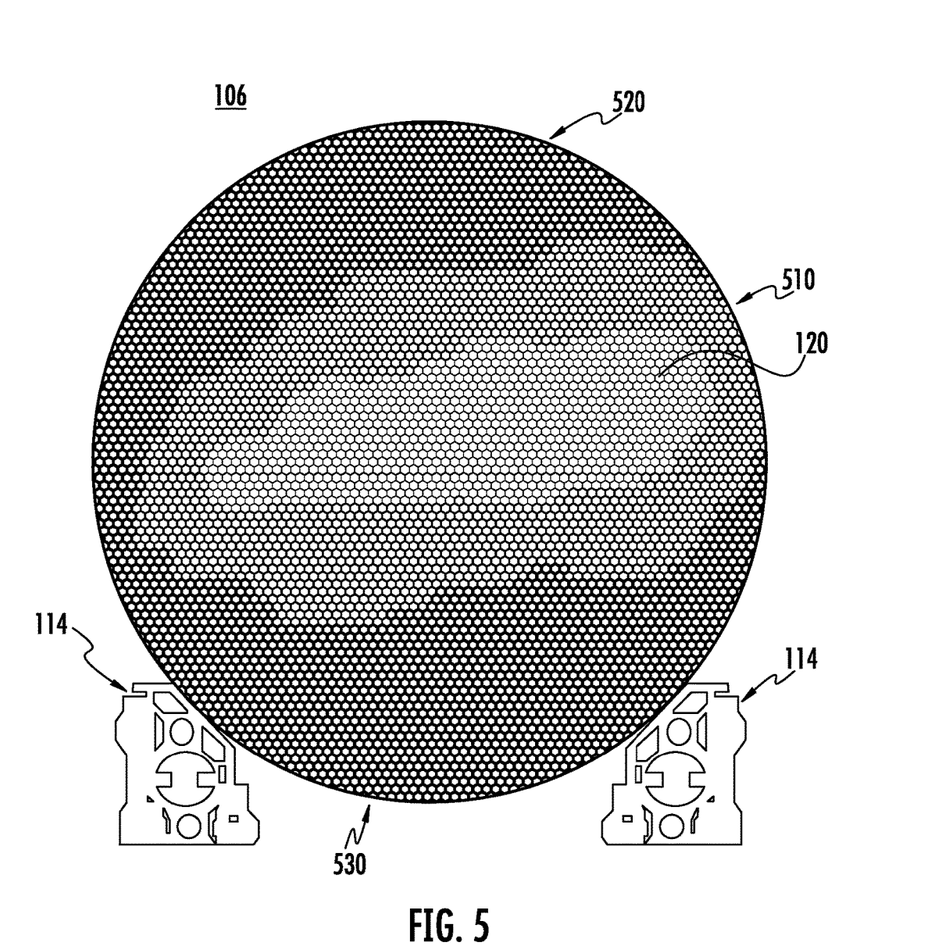
FIG. 5 shows an end view of a part in the support chuck of the inspection apparatus looking toward the diffuse light source according to exemplary embodiments of the disclosure.

FIG. 5 shows an outlet end view of a part 106 in the support chuck 114 of the inspection apparatus 100 looking toward the light source 102 according to exemplary embodiments of the disclosure. FIG. 5 illustrates how channel walls 120 may not be completely parallel with each other. The bright portion 510 across the middle of the part 106 from the upper right to the lower left of the drawing indicates light 108 transmitted through the channels. On the other hand, dark portions 520 at the upper part of the drawing and 530 at the lower part of the drawing indicate the light 104 is blocked by channel walls 120.

Figure 6A:
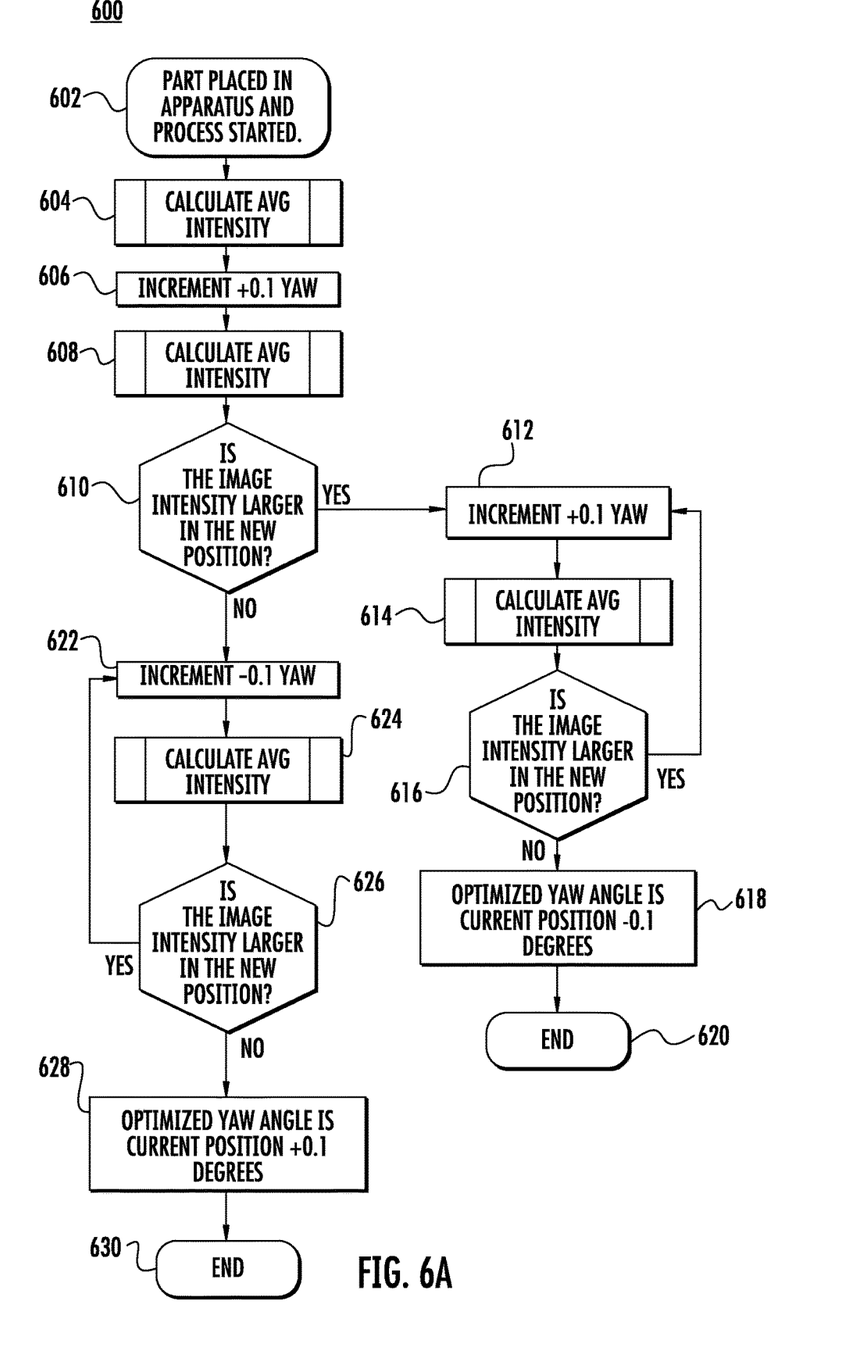
FIG. 6A is a schematic flow chart diagram of an example method to align yaw of a ceramic honeycomb body in an inspection apparatus according to exemplary embodiments of the disclosure.

FIG. 6A is a schematic flow chart diagram of an example method 600 to align yaw of a ceramic honeycomb body 106 in an inspection apparatus 100 according to exemplary embodiments of the disclosure. Referring back to FIGS. 1, 3, and 4, the inspection apparatus 100 may perform the exemplary embodiment of the disclosed method 600 to align yaw of the ceramic honeycomb body 106. In operation 602 a part 106 is placed in apparatus 100, such as on support chuck 114 and horizontal reference angle 122 is noted, for example by controller 118. In operation 604 an average intensity of transmitted light 108 is calculated by controller 118.

In operation 606, the controller 118 controls the support chuck 114 to increment the part by an angular increment, such as by plus 0.1 degree (+0.1°) yaw. The average intensity of transmitted light 108 is calculated at the new yaw position by the controller 118 in operation 608. The controller 118 compares the average intensity of transmitted light 108 at the new yaw position to a stored value of the average intensity of transmitted light 108 at the previous yaw position at operation 610. When the average intensity of transmitted light 108 at the new yaw position is greater than the stored value of the average intensity of transmitted light 108 at the previous yaw position, operation 612 increments the part by the yaw angular increment (+0.1°).

Operation 614 again calculates the average intensity of transmitted light 108 at the new yaw position and in operation 616 the controller 118 compares the average intensity of transmitted light 108 at the new yaw position to a stored value of the average intensity of transmitted light 108 at the previous yaw position. When the average intensity of transmitted light 108 at the new yaw position is greater than the stored value of the average intensity of transmitted light 108 at the previous yaw position calculated in operation 616, operation 612 increments the part by the yaw angular increment (+0.1°). Operations 614 and 616 repeat.

When the average intensity of transmitted light 108 at the new yaw position is less than the stored value of the average intensity of transmitted light 108 at the previous yaw position calculated in operation 616, operation 618 increments the part back to the previous yaw position, for example, by the negative yaw angular increment (−0.1°). The yaw position determined by operation 618 is determined to be the yaw reference angle 122 aligned to the reference axis and the process 600 ends at 620.

Referring back to operation 610, when the controller 118 compares the average intensity of transmitted light 108 at the new yaw position to a stored value of the average intensity of transmitted light 108 at the previous yaw position at operation 610 and the average intensity of transmitted light 108 at the new yaw position is less than the stored value of the average intensity of transmitted light 108 at the previous yaw position, operation 622 increments the part back to the previous yaw position, for example, by the negative yaw angular increment (−0.1°). Operation 624 calculates the average intensity of transmitted light 108 at the new yaw position and in operation 626 the controller 118 compares the average intensity of transmitted light 108 at the new yaw position to a stored value of the average intensity of transmitted light 108 at the previous yaw position.

When the average intensity of transmitted light 108 at the new yaw position is greater than the stored value of the average intensity of transmitted light 108 at the previous yaw position calculated in operation 626, operation 622 increments the part by the negative yaw angular increment (−0.1°). Operations 624 and 626 repeat. When the average intensity of transmitted light 108 at the new yaw position is less than the stored value of the average intensity of transmitted light 108 at the previous yaw position calculated in operation 626, operation 628 increments the part back to the previous yaw position, for example, by the positive yaw angular increment (+0.1°). The yaw position determined by operation 628 is determined to be the yaw reference angle 122 aligned to the reference axis and the process 600 ends at 630.

FIG. 6A illustrates a hill climb method of determining yaw alignment. Other methods to determine yaw alignment may include, for example, such methods as the downhill simplex or amoeba method.

Figure 6B:
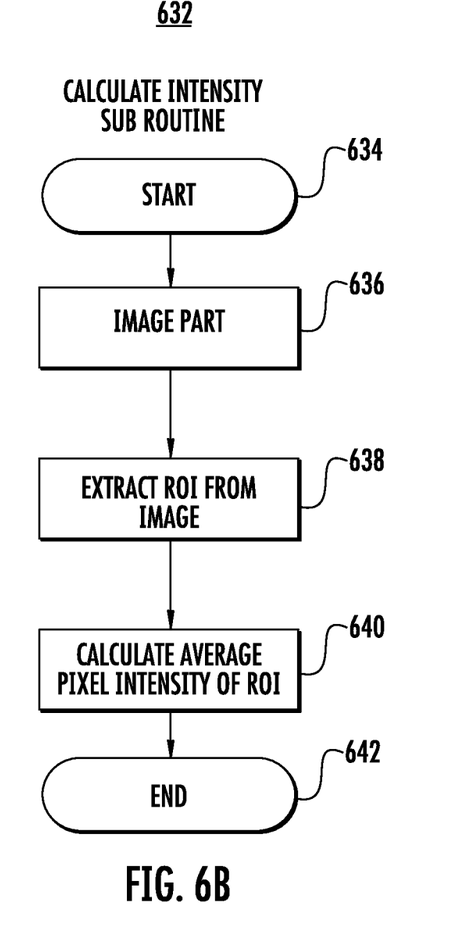
FIG. 6B is a schematic flow chart diagram of a method to calculate average light intensity in an example alignment method of a ceramic honeycomb body in an inspection apparatus according to exemplary embodiments of the disclosure.

FIG. 6B is a schematic flow chart diagram of a method to calculate average light intensity 632 in the example alignment method 600 to align yaw of a ceramic honeycomb body 106 according to exemplary embodiments of the disclosure. Process 632 starts at operation 634 and an image of the part 106 is captured, for example, by camera 112, in operation 636. An example of a captured image is shown in FIG. 5 where an outlet end view of a part 106 in the support chuck 114 of the inspection apparatus 100 looking toward the diffuse light source 102 is captured according to exemplary embodiments of the disclosure. The process to calculate average light intensity 632 can be performed in yaw alignment process 600 at operations 604, 608, 614, and 624. In operation 638 of the method to calculate average light intensity 632 the region of interest (ROI) is extracted from the image, for example, by controller 118. In operation 640, the controller 118 calculates and returns an average pixel intensity of the ROI. Process 632 ends at operation 642.

Figure 6C:
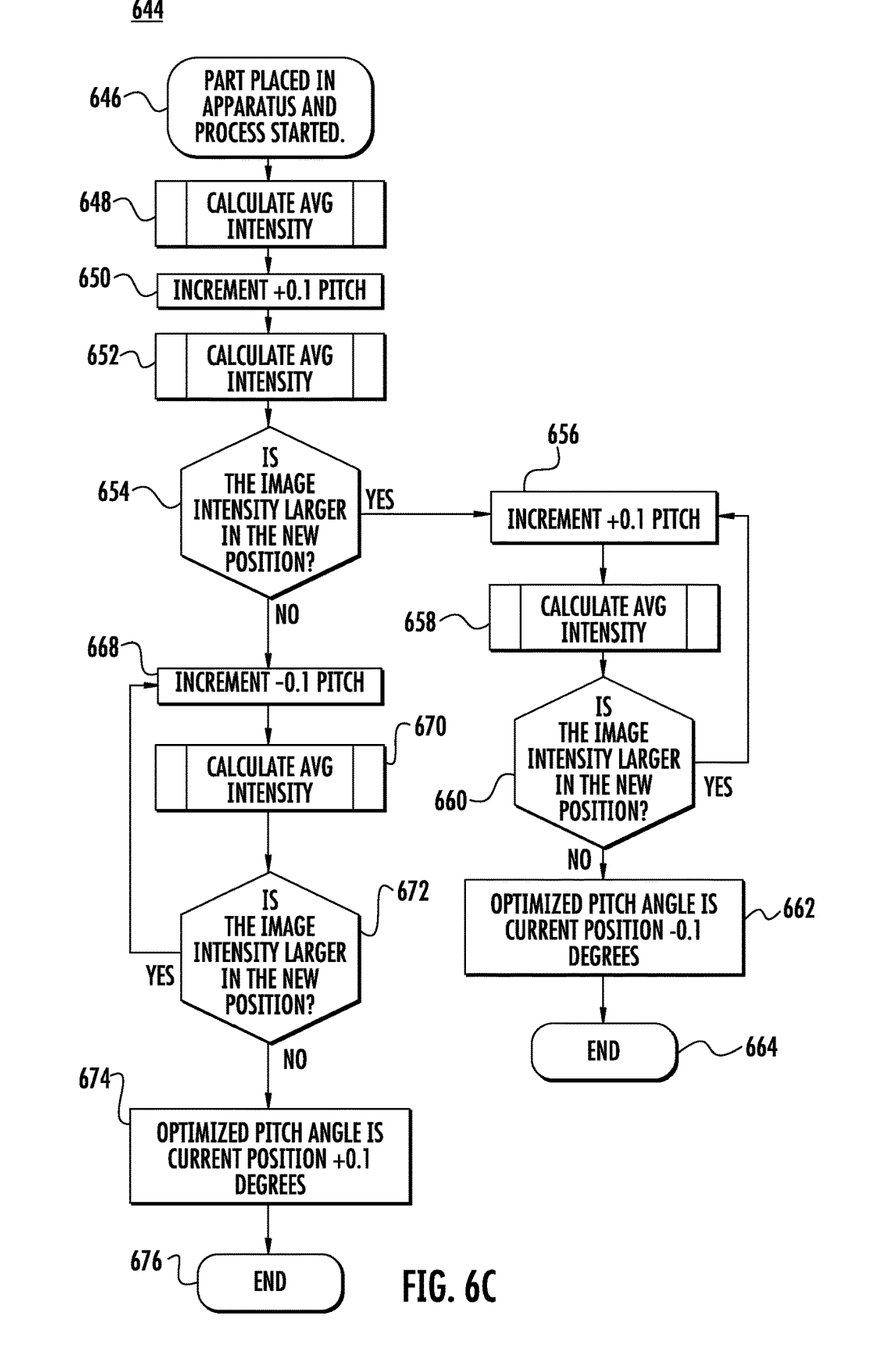
FIG. 6C is a schematic flow chart diagram of an example method to align pitch of a ceramic honeycomb body in an inspection apparatus according to exemplary embodiments of the disclosure.

FIG. 6C is a schematic flow chart diagram of an example method 644 to align pitch of a ceramic honeycomb body 106 in an inspection apparatus 100 according to exemplary embodiments of the disclosure. In operation 646 a part 106 is placed in apparatus 100, such as on support chuck 114 and vertical reference angle 116 is noted, for example by controller 118. In operation 648 an average intensity of transmitted light 108 is calculated by controller 118. The method to calculate average light intensity 632 illustrated in FIG. 6B and described above may be used in this example alignment method 644 according to exemplary embodiments of the disclosure.

In operation 650, the controller 118 controls the support chuck 114 to increment the part by an angular increment, such as by plus 0.1 degree (+0.1°) pitch. The average intensity of transmitted light 108 is calculated at the new pitch position by the controller 118 in operation 652. The controller 118 compares the average intensity of transmitted light 108 at the new pitch position to a stored value of the average intensity of transmitted light 108 at the previous pitch position at operation 654. When the average intensity of transmitted light 108 at the new pitch position is greater than the stored value of the average intensity of transmitted light 108 at the previous pitch position, operation 656 increments the part by the pitch angular increment (+0.1°).

Operation 658 again calculates the average intensity of transmitted light 108 at the new pitch position and in operation 660 the controller 118 compares the average intensity of transmitted light 108 at the new pitch position to a stored value of the average intensity of transmitted light 108 at the previous pitch position. When the average intensity of transmitted light 108 at the new pitch position is greater than the stored value of the average intensity of transmitted light 108 at the previous pitch position calculated in operation 660, operation 656 increments the part by the pitch angular increment (+0.1°). Operations 658 and 660 repeat.

When the average intensity of transmitted light 108 at the new pitch position is less than the stored value of the average intensity of transmitted light 108 at the previous pitch position calculated in operation 660, operation 662 increments the part back to the previous pitch position, for example, by the negative pitch angular increment (−0.1°). The pitch position determined by operation 662 is determined to be the pitch reference angle 116 aligned to the reference axis and the process ends at 664.

Referring back to operation 654, when the controller 118 compares the average intensity of transmitted light 108 at the new pitch position to a stored value of the average intensity of transmitted light 108 at the previous pitch position at operation 654 and the average intensity of transmitted light 108 at the new pitch position is less than the stored value of the average intensity of transmitted light 108 at the previous pitch position, operation 668 increments the part back to the previous pitch position, for example, by the negative pitch angular increment (−0.1°). Operation 670 calculates the average intensity of transmitted light 108 at the new pitch position and in operation 672 the controller 118 compares the average intensity of transmitted light 108 at the new pitch position to a stored value of the average intensity of transmitted light 108 at the previous pitch position.

When the average intensity of transmitted light 108 at the new pitch position is greater than the stored value of the average intensity of transmitted light 108 at the previous pitch position calculated in operation 672, operation 668 increments the part by the negative pitch angular increment (−0.1°). Operations 670 and 672 repeat. When the average intensity of transmitted light 108 at the new pitch position is less than the stored value of the average intensity of transmitted light 108 at the previous pitch position calculated in operation 672, operation 674 increments the part back to the previous pitch position, for example, by the positive pitch angular increment (+0.1°). The pitch position determined by operation 674 is determined to be the pitch reference angle 116 aligned to the reference axis and the process ends at 676.

FIG. 6C illustrates a hill climb method of determining pitch alignment. Other methods to determine pitch alignment may include, for example, such methods as the downhill simplex or amoeba method.

The schematic flow chart diagram of a method to calculate average light intensity 632 of FIG. 6B can be used in the example alignment method 644 to align pitch of a ceramic honeycomb body 106 according to exemplary embodiments of the disclosure. The process to calculate average light intensity 632 can be performed in pitch alignment process 644 at operations 648, 652, 658, and 670.

While the yaw and pitch alignment has been described with respect to moving the position of the part 106, this disclosure is not so limited. It is also possible to control the angular position of the lens 110 while the part 106 remains stationary according to exemplary embodiments of the disclosure. Controlling the position of the lens 110 by following a method similar to that described above with reference to FIGS. 6A, 6B, and 6C, can produce the same results as controlling the position of the part 106 being imaged to align the part 106 with the optical axis of the lens 110. In such an embodiment, the lens can be controlled by the controller 118 to move in the pitch and yaw directions.

The pitch 116 and yaw 122 angles have been described with respect to a side view and a top view, respectively, however, the pitch and yaw angles 116, 122 can be at any orientation. Generally, the pitch angle 116 and yaw angle 122 are orthogonal to one another. While terms, top, side, vertical, and horizontal are used, the disclosure is not so limited to these exemplary embodiments. Instead, spatially relative terms, such as "top", "bottom", "horizontal", "vertical", "side", "beneath", "below", "lower", "above", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the exemplary term "below" can encompass both an orientation of above and below. The device may be otherwise oriented (rotated 90 degrees or at other orientations) and the spatially relative descriptors used herein interpreted accordingly. Thus, the exemplary term "side" can become "top" and vice versa when the inspection apparatus in FIG. 1 is rotated 90 degrees.

Once the position (pitch 116 and yaw 122 angles) where the part 106 is aligned with the imaging system (optical axis of lens 110) is established, that is, where the average (mean) intensity of an evenly illuminated image of the part 106 is maximized, this information may be used to inspect the part for internal defects. The position (pitch 116 and yaw 122 angles) of the part 106 aligned with the imaging system (optical axis of lens 110) is referred to herein as the alignment angle. This alignment angle is an optimal viewing angle for some defects. It is also a reference location, which can be used to determine how to view other defects for which it is not the optimal viewing angle. The controller 118 can control the entire process, including image capture, analysis of the image to determine the average intensity, motion required for the alignment process, and capturing and analyzing images for defect detection.

Ceramic honeycomb structures 106 may exhibit several types of internal defects which are detectable using the inspection apparatus 100 according to exemplary embodiments of the disclosure. Internal cracks, which may occur during firing, are areas where the cell walls of many adjacent cells have cracked. Internal tears can be caused by areas of uneven batch flow through the die during extrusion, which appear as a "wasp nest" inside the part 106 when viewed from an outlet end looking toward the light source 102.

Swollen webs can also be caused by uneven batch flow through the die during extrusion and can be seen as thick webs in an image from camera 112 in apparatus 100. Dead channels are a defect which is caused by poor formation of the peripheral cells of the part 106, leading to their blockage during the skinning process. This disclosure provides methods and apparatus for automated inspection of ceramic honeycomb structures for at least one of these defects (cracks, tears, swollen webs, dead channels, etc.).

A defect specific inspection technique may be employed for each of the different types of possible defects. For example, an internal crack, when imaged from the alignment angle with the apparatus 100 described herein, can appear as a faint line across the face of the part 106. If the alignment of the part is then displaced from the alignment angle in a direction which has some component normal (90°) to the line representing the crack, then the contrast of the crack in the image will be improved. The crack will begin to appear to cast a shadow over the face of the part. An example of this can be seen in FIGS. 7A and 7B.

Figure 7A:
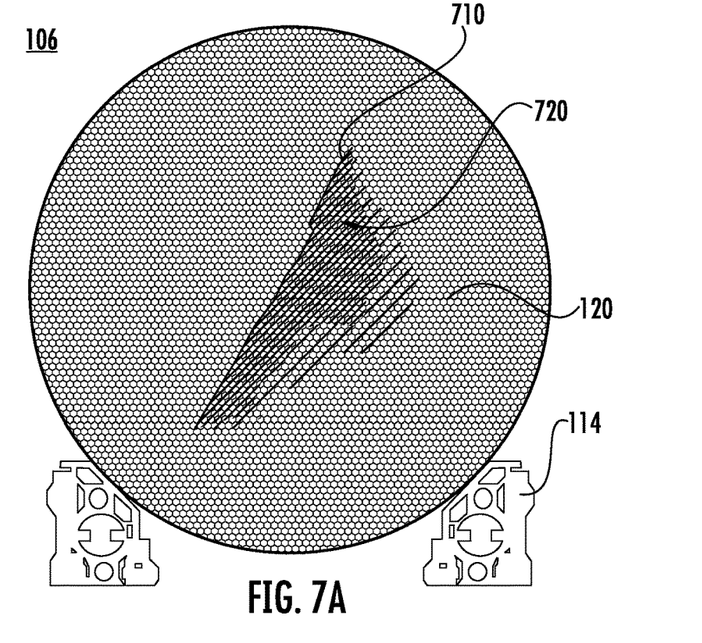
FIG. 7A shows an end view of a part having a defect in the support chuck of the inspection apparatus looking toward the diffuse light source according to exemplary embodiments of the disclosure.
Figure 7B:
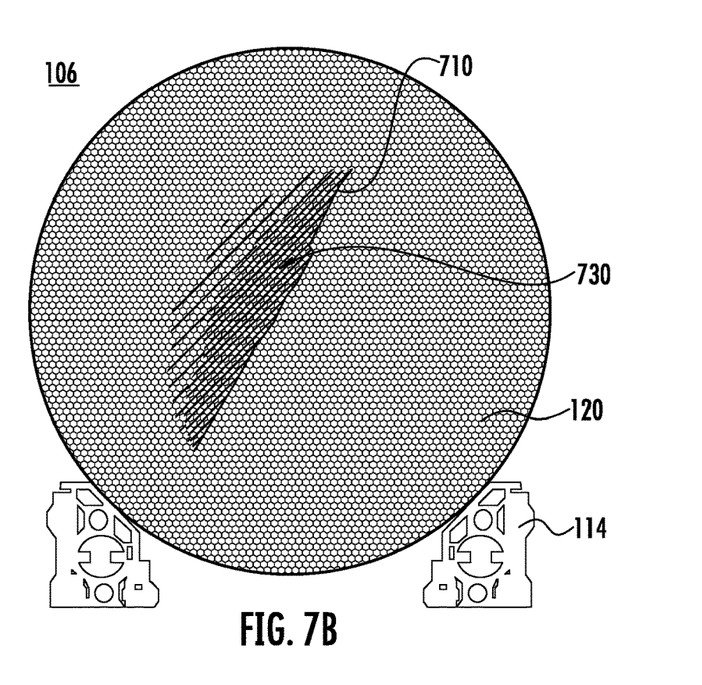
FIG. 7B shows an end view of the part having a defect shown in FIG. 7A after yaw rotation according to exemplary embodiments of the disclosure.

FIG. 7A shows an outlet end view of a part 106 having a defect 710 (crack) in the support chuck 114 of the inspection apparatus 100 looking toward the diffuse light source 102 according to exemplary embodiments of the disclosure. If the part 106 is rotated so that the face of the part 106 is seen to move to the right (a change in yaw angle), the shadow 720 will slowly disappear and then reappear with the shadow 730 on the left side of the crack 710. FIG. 7B shows an end view of the part 106 having the crack defect 710 shown in FIG. 7A after yaw rotation according to exemplary embodiments of the disclosure.

The shadow 730 can exhibit a sharp gradient on a border in a direction which is known based on the direction in which the part 106 was moved from the alignment angle. When the part 106 is subjected to a positive displacement along the yaw axis, then the crack 710 shadow 730 will show a large negative gradient in the image. When the part 106 is subjected to a negative displacement along the yaw axis from the alignment angle, then the crack 710 shadow 720 will show a large positive gradient. The controller 118 can process an image and check for the presence of one gradient and the absence of the other. The displacement angle can then be negated (the part 106 moved the same distance from the alignment angle in the opposite direction) and the controller can again check for the presence of the expected gradient and absence of the other. This behavior is unique among features seen when imaging cellular ceramic substrates. Thus, the inspection apparatus 100 can detect internal cracks with excellent repeatability and accuracy. This type of inspection and detection is possible after first determining the alignment angle using the inspection apparatus 100 according to these exemplary embodiments.

The inspection apparatus 100 according to these exemplary embodiments may also be used to similarly detect other internal defects common in extruded cellular ceramic substrates. According to these exemplary embodiments the apparatus and method described herein can repeatability and automatically inspect honeycomb bodies 106.

Additionally, determination of the alignment angle reference allows the inspection apparatus 100 to capture images at angles relative to the alignment angle to locally maximize the contrast of the image. This may be necessary when imaging substrates 106 such as the one seen in FIG. 5. The support 114 may be manipulated by the controller 118 to illuminate the dark portions 520, 530 in a part 106 like the one seen in FIG. 5 by making small angular displacements around the alignment angle. That is, a first alignment angle may be established where bright portion 510 is the maximized average brightness of the part 106 image, that is the entire face of the part 106. However, a second alignment angle may also be established where an average brightness is maximized in dark portion 520. Further, a third alignment angle may be established where an average brightness is maximized in dark portion 530. Portions 510, 520, and 530 may be arbitrarily distributed from part to part. Therefore, the part face may be consistently divided into two or more sectors and alignment angles established for each sector such that every channel is within a sector and within an maximized average bright portion when the sector is aligned at the sector alignment angle.

The sector alignment angles can be established in a similar manner to establishing the alignment angle from the images captured at angles relative to the alignment angle. The part 106 can be imaged by a composite image of maximized average brightness in each sector where each image in the composite image covers a sector of the part 106 end face. For example, the imaged part 106 may be imaged with sixteen sectors where each sector has a maximized average brightness and associated sector alignment angle. In this instance the image is divided into sixteen "pie slices". The inspection process can inspect each sector about each sector specific alignment angle to detect defects. That is, the apparatus and process can search all images captured to find which image produces the best contrast for each "pie slice". The highest contrast pie slice is then searched for internal defects such as cracks, internal tears, internal swollen webs, or dead channels. The number of sections is not particularly limited and can be, for example, between two and sixty-four.

EXAMPLES

The disclosure is further described below with respect to certain exemplary and specific embodiments thereof, which are illustrative only and not intended to be limiting. In accordance with some of the examples, a prototype of an inspection apparatus 100 according to exemplary embodiments of the disclosure comprising a diffuse light source 102, a telecentric lens 110, a camera 112 comprising a detector, a honeycomb body support chuck 114, and a controller 118, as described herein, for example, with reference to FIGS. 1-4 was implemented. The inspection apparatus 100 was used for automated internal inspection of heavy duty substrates 106 and provided improved repeatability and accuracy compared to manual inspection with a light box. As set forth in Table 1, "kappa within appraisers" is a measure of the repeatability of the apparatus 100. "Kappa appraisers vs. standard" is a measure of the agreement between the inspection apparatus 100 and reference values determined by a quality standard. The quality standard was established by a quality department. Essentially, "kappa" is a rescaled percent agreement with a standard having agreement due to chance removed. The higher kappa value means that the inspection apparatus 100 according to exemplary embodiments of the disclosure agreed more often with the reference value. In other words, a higher "kappa appraisers vs. standard" value means the inspection apparatus 100 is more accurate.

The data was obtained by running an experiment with the prototype apparatus 100. Twenty eight parts 106 were characterized by the quality department as pass or fail (Ref). These parts 106 were then run on the inspection apparatus 100 for three repetitions (Rep) each. For each repetition, it was recorded whether the apparatus 100 passed or failed (P/F) the part 106. The apparatus 100 also identified the type of defect as the "Reason" for the fails. This data is presented in Table 2. Statistical analysis was then used to calculate the "kappa within appraisers" and "kappa appraisers vs. standard values."

TABLE 1

|  | Apparatus 100 | operator |
|---|---|---|
| kappa within appraisers | 0.74 | 0.61-0.70 |
| kappa appraisers vs. standard | 0.70 | 0.3 |

TABLE 2

| Run | Example—Rep | Ref P/F | Apparatus 100 P/F | Apparatus 100 Reason |
|---|---|---|---|---|
| 1 | 119-1 | Fail | Fail | ContiguousInternalTear |
| 2 | 119-2 | Fail | Fail | ContiguousInternalTear |
| 3 | 119-3 | Fail | Fail | ContiguousInternalTear |
| 4 | 121-1 | Fail | Fail | InternalCrack |
| 5 | 121-2 | Fail | Fail | InternalCrack |
| 6 | 121-3 | Fail | Fail | InternalCrack |
| 7 | 131-1 | Pass | Pass | None |
| 8 | 131-2 | Pass | Pass | None |
| 9 | 131-3 | Pass | Pass | None |
| 10 | 134-1 | Fail | Fail | ContiguousInternalTear |
| 11 | 134-2 | Fail | Pass | None |
| 12 | 134-3 | Fail | Fail | ContiguousInternalTear |
| 13 | 188-1 | Pass | Fail | ContiguousInternalTear |
| 14 | 188-2 | Pass | Fail | ContiguousBlockedCellArea |
| 15 | 188-3 | Pass | Fail | ContiguousInternalTear |
| 16 | 202-1 | Fail | Fail | ContiguousInternalTear |
| 17 | 202-2 | Fail | Fail | ContiguousInternalTear |
| 18 | 202-3 | Fail | Fail | ContiguousInternalTear |
| 19 | 217-1 | Pass | Pass | None |
| 20 | 217-2 | Pass | Pass | None |
| 21 | 217-3 | Pass | Pass | None |
| 22 | 223-1 | Fail | Fail | InternalCrack |
| 23 | 223-2 | Fail | Fail | InternalCrack |
| 24 | 223-3 | Fail | Fail | InternalCrack |
| 25 | 227-1 | Pass | Pass | None |
| 26 | 227-2 | Pass | Pass | None |
| 27 | 227-3 | Pass | Fail | DeadChannel |
| 28 | 273-1 | Pass | Pass | None |
| 29 | 273-2 | Pass | Pass | None |
| 30 | 273-3 | Pass | Pass | None |
| 31 | 315-1 | Fail | Fail | InternalCrack |
| 32 | 315-2 | Fail | Fail | InternalCrack |
| 33 | 315-3 | Fail | Fail | InternalCrack |
| 34 | 330-1 | Fail | Fail | ContiguousInternalTear |
| 35 | 330-2 | Fail | Fail | ContiguousInternalTear |
| 36 | 330-3 | Fail | Fail | ContiguousInternalTear |
| 37 | 362-1 | Fail | Fail | ContiguousInternalTear |
| 38 | 362-2 | Fail | Fail | ContiguousInternalTear |
| 39 | 362-3 | Fail | Fail | ContiguousInternalTear |
| 40 | 368-1 | Fail | Pass | None |
| 41 | 368-2 | Fail | Fail | InternalCrack |
| 42 | 368-3 | Fail | Fail | InternalCrack |
| 43 | 381-1 | Fail | Fail | InternalCrack |
| 44 | 381-2 | Fail | Fail | InternalCrack |
| 45 | 381-3 | Fail | Fail | ContiguousInternalTear |
| 46 | 500-1 | Fail | Fail | InternalCrack |
| 47 | 500-2 | Fail | Fail | InternalCrack |
| 48 | 500-3 | Fail | Fail | InternalCrack |
| 49 | 501-1 | Fail | Fail | DeadChannel |
| 50 | 501-2 | Fail | Fail | DeadChannel |
| 51 | 501-3 | Fail | Fail | DeadChannel |
| 52 | 505-1 | Fail | Fail | ContiguousInternalTear |
| 53 | 505-2 | Fail | Fail | ContiguousInternalTear |
| 54 | 505-3 | Fail | Fail | ContiguousInternalTear |
| 55 | 507-1 | Pass | Pass | None |
| 56 | 507-2 | Pass | Fail | DeadChannel |
| 57 | 507-3 | Pass | Pass | None |
| 58 | 515-1 | Pass | Pass | None |
| 59 | 515-2 | Pass | Pass | None |
| 60 | 515-3 | Pass | Pass | None |
| 61 | 524-1 | Fail | Fail | DeadChannel |
| 62 | 524-2 | Fail | Fail | DeadChannel |
| 63 | 524-3 | Fail | Fail | DeadChannel |
| 64 | 525-1 | Pass | Fail | DeadChannel |
| 65 | 525-2 | Pass | Fail | DeadChannel |
| 66 | 525-3 | Pass | Fail | DeadChannel |
| 67 | 526-1 | Pass | Pass | None |
| 68 | 526-2 | Pass | Pass | None |
| 69 | 526-3 | Pass | Pass | None |
| 70 | 600-1 | Fail | Fail | InternalCrack |
| 71 | 600-2 | Fail | Fail | InternalCrack |
| 72 | 600-3 | Fail | Fail | InternalCrack |
| 73 | 700-1 | Fail | Fail | InternalCrack |
| 74 | 700-2 | Fail | Fail | InternalCrack |
| 75 | 700-3 | Fail | Fail | InternalCrack |
| 76 | 889-1 | Fail | Fail | DeadChannel |
| 77 | 889-2 | Fail | Fail | ContiguousInternalTear |
| 78 | 889-3 | Fail | Fail | ContiguousInternalTear |

False Fail (Alpha Risk). Data in Table 2 shows two Examples, 188 and 525, disagreed on all three Reps with the Ref returning a fail for the parts 106 deemed passed by Ref. Two additional Examples had one Rep each, 227-3 and 507-2, that gave a fail to the parts 106 deemed passed by Ref.

Reason Disagreement. Two Examples, 381 and 505, and two Reps of a third Example, 368 (Reps 368-2 and 368-3), had agreement with Ref on failing the part 106, but the reason for the fail, internal crack, contiguous internal tear, did not agree with Ref.

False Pass (Beta Risk). An additional Example, 134, had one Rep, 134-2, that gave a pass to a part 106 that was deemed failed by Ref. Rep 1 of Example 368 mentioned above under Reason Disagreement also exhibited a pass when Ref had deemed the part 106 a fail.

Advantages of the apparatus and methods of inspecting honeycomb bodies provided in accordance with the present disclosure include economical automated alignment and inspection of ceramic honeycomb structures. That is, alignment and inspection use the same hardware, which provides manufacturing cost savings and efficiencies. Exemplary embodiments of the disclosure provide repeatable images of defects for repeatable image analysis and defect detection. To obtain repeatable images, exemplary embodiments of the disclosure provide the orientation in space of the parallel channels of the part in a way which is repeatable and accurate. Exemplary embodiments of the disclosure provide a method and apparatus for aligning a ceramic substrate with the optical axis of a machine vision inspection system in a way which is accurate and repeatable. Exemplary embodiments of the disclosure also provide improved alignment for large ceramic honeycomb structures. The disclosed apparatus and methods take into account poor parallelism of channels in large parts and determine the optimal alignment with high repeatability. Use of a telecentric lens or Fresnel lens provides the advantage of allowing the alignment of the greatest number of channels of the ceramic substrate along the optical axis of the imaging system. This allows efficient and robust inspection of more non-parallel channels of the substrate, which become more frequent as the size of the substrates increase.

Exemplary embodiments of the disclosure to detect internal cracks and non-crack internal defects in ceramic substrates by capturing and analyzing multiple images as described herein, improves accuracy and repeatability of the inspection over other techniques, such as single image techniques and manual inspection. Another advantage of the apparatus and methods of inspecting honeycomb bodies provided in accordance with the present disclosure is that the face of the honeycomb body does not have to be perpendicular to the channels to determine the alignment angle.

It will be understood that for the purposes of this disclosure, "at least one of X, Y, and Z" can be construed as X only, Y only, Z only, or any combination of two or more items X, Y, and Z (e.g., XYZ, XYY, YZ, ZZ).

Reference throughout this specification to exemplary embodiments and similar language throughout this specification may, but do not necessarily, refer to the same embodiment. Furthermore, the described features, structures, or characteristics of the subject matter described herein with reference to an exemplary embodiment may be combined in any suitable manner in one or more exemplary embodiments.

It will be apparent to those skilled in the art that various modifications and variations can be made in the present disclosure without departing from the spirit or scope of the disclosure. Thus, it is intended that the appended claims cover the modifications and variations of this disclosure provided they come within the scope of the appended claims and their equivalents.

The invention claimed is:

1. An inspection apparatus to inspect a ceramic honeycomb body, the apparatus comprising:
    a light source configured to direct light into channels of the ceramic honeycomb body;
    a lens configured to receive at least a portion of the light transmitted through channels of the ceramic honeycomb body;
    an imaging device configured to capture images of the transmitted light;
    a support chuck configured to support the honeycomb body; and
    a controller configured to receive the captured images, to analyze each captured image, to determine an alignment angle at which the channels and an optical axis of the lens are aligned based on analysis of the captured images, and to align the channels and the optical axis of the lens by adjusting at least one of the support chuck and the lens based on the determined alignment angle.

2. The apparatus of claim 1, wherein the light source comprises a diffuse light source.

3. The apparatus of claim 1, wherein the lens comprises at least one of a telecentric lens and a Fresnel lens.

4. The apparatus of claim 1, wherein the controller is configured to adjust at least one of the support chuck and the lens to effect alignment of the channels and the lens optical axis to detect at least one defect in the honeycomb body.

5. The apparatus of claim 4, wherein the at least one defect comprises at least one of internal crack, an internal tear, a swollen web, and a dead channel.

6. The apparatus of claim 1, wherein the controller is configured to analyze each captured image to determine average transmitted light intensity of the respective captured image; and
    wherein the controller is configured to align the channels and the optical axis of the lens where the average transmitted light intensity is maximized.

7. The apparatus of claim 1, wherein the imaging device comprises a camera comprising a detector to capture images of the transmitted light.

8. The apparatus of claim 1, further comprising a transport device configured to place the ceramic honeycomb body on the support chuck, wherein the channels and the lens optical axis are out of alignment with respect to at least one of a yaw angle and a pitch angle.

9. The apparatus of claim 1, wherein the controller is configured to, for each of a plurality of sectors of the channels, determine an alignment angle at which the respective sector and the optical axis of the lens are aligned based on the analysis of the captured images, and to align the sectors and the optical axis of the lens by adjusting at least one of the support chuck and the lens based on the determined alignment angles, wherein each sector comprises at least one channel not parallel to one other of the sectors.

10. The apparatus of claim 9, wherein the number of sectors is between 2 and 64.

11. The apparatus of claim 10, wherein the controller is configured to adjust at least one of the support chuck and the lens to tilt the channels about each sector alignment to detect at least one defect in that sector.

12. An apparatus to manufacture a ceramic honeycomb body, the apparatus comprising:
    an inspection apparatus, comprising:
        a light source configured to direct light into channels of the ceramic honeycomb body;
        a lens configured to receive at least a portion of the light transmitted through channels of the ceramic honeycomb body;
        an imaging device configured to capture images of the transmitted light;
        a support chuck configured to support the honeycomb body; and
        a controller configured to receive the captured images, to analyze each captured image, to determine an alignment angle at which the channels and an optical axis of the lens are aligned based on analysis of the captured images, and to align the channels and the optical axis of the lens by adjusting at least one of the support chuck and the lens based on the determined alignment angle.

13. A method of inspecting a ceramic honeycomb body, the method comprising:
    directing light toward a first end of the ceramic honeycomb body, at least a portion of the light transmitted through channels of the ceramic honeycomb body;
    imaging the portion of light through a lens, the imaging comprising capturing a plurality of images at incremental angles between the channels and an optical axis of the lens;
    determining an alignment angle at which the channels and the optical axis of the lens are aligned by analyzing at least a portion of the captured images; and
    aligning the channels and the optical axis of the lens by adjusting at least one of the ceramic honeycomb body and the lens based on the determined alignment angle.

14. The method of claim 13, further comprising adjusting at least one of the channels and the lens optical axis alignment about the alignment angle to detect at least one defect in the honeycomb body.

15. The method of claim 14, wherein the at least one defect comprises at least one of an internal crack, an internal tear, a swollen web, and a dead channel.

16. The method of claim 13, further comprising recording at least one of an identifier of the ceramic honeycomb body and a type of a defect in response to the defect being detected.

17. The method of claim 13, wherein determining the alignment angle comprises:

analyzing at least the portion of the captured images to determine an average transmitted light intensity of each captured image in at least the portion; and determining the alignment angle to be the incremental angle at which the average transmitted light intensity is maximized.

18. The method of claim 13, wherein determining the alignment angle comprises:

analyzing images for a sector of the ceramic honeycomb body, the ceramic honeycomb body having a plurality of sectors, each sector including at least one channel that is not parallel to a channel in at least one other sector; and wherein aligning the channels and the optical axis of the lens comprises:

aligning the sector for which the images are analyzed and the optical axis of the lens.

19. The method of claim 18, further comprising adjusting at least one of the channels and lens optical axis alignment about each sector alignment to detect at least one defect in that sector.

20. A method of manufacturing a ceramic honeycomb body, the method comprising:

inspecting the ceramic honeycomb body, comprising:

directing light toward a first end of the ceramic honeycomb body, at least a portion of the light transmitted through channels of the ceramic honeycomb body;

imaging the portion of light through a lens, the imaging comprising capturing a plurality of images at incremental angles between the channels and an optical axis of the lens;

determining an alignment angle at which the channels and the optical axis of the lens are aligned by analyzing at least a portion of the captured images; and aligning the channels and the optical axis of the lens by adjusting the ceramic honeycomb body based on the determined alignment angle.

* * * * *

UNITED STATES PATENT AND TRADEMARK OFFICE
CERTIFICATE OF CORRECTION

| | |
|---|---|
| PATENT NO. | : 10,145,805 B2 |
| APPLICATION NO. | : 15/528919 |
| DATED | : December 4, 2018 |
| INVENTOR(S) | : Alan Russell Stanford et al. |

It is certified that error appears in the above-identified patent and that said Letters Patent is hereby corrected as shown below:

In the Specification

In Column 1, Lines 5-6, delete "PCT/US2015/06147," and insert -- PCT/US2015/061471, --, therefor.

In Column 1, Line 9, delete "2014" and insert -- 2014, the --, therefor.

Signed and Sealed this
First Day of August, 2023

Katherine Kelly Vidal
*Director of the United States Patent and Trademark Office*